(12) United States Patent
Ferrari

(10) Patent No.: US 7,846,430 B2
(45) Date of Patent: Dec. 7, 2010

(54) COMPOSITION AND METHOD FOR TREATING BOVINE PAPILLOMA VIRUS IN EQUINE

(76) Inventor: Stefano Ferrari, c/o Saint Simeon LDA, 437 Route 308, Rhinebeck, NY (US) 12572

( * ) Notice: Subject to any disclaimer, the term of this patent is extended or adjusted under 35 U.S.C. 154(b) by 0 days.

(21) Appl. No.: 12/039,948

(22) Filed: Feb. 29, 2008

(65) Prior Publication Data

US 2008/0213242 A1 Sep. 4, 2008

Related U.S. Application Data

(60) Provisional application No. 60/892,573, filed on Mar. 2, 2007.

(51) Int. Cl.
*A61K 38/47* (2006.01)
(52) U.S. Cl. .................................... 424/94.61; 424/94.6
(58) Field of Classification Search ........................ None
See application file for complete search history.

(56) References Cited

U.S. PATENT DOCUMENTS 5,019,411 A * 5/1991 Johnson et al. ............... 426/52
6,147,086 A * 11/2000 Brenman ..................... 514/293
2005/0008631 A1 * 1/2005 Lee-Huang et al. ....... 424/94.61

OTHER PUBLICATIONS

CDC Fact Sheet "Genital HPV" Dec. 2007 (2 pages), retrieved from URL: <http://www.cdc.gov/STD/HPV/STDFact-HPV.htm> on Nov. 18, 2009.*
de Villiers et al, "Classification of papillomaviruses" Virology, 2004, vol. 324, pp. 17-27.*
Schiffman et al, "Human Papillomavirus: Epidemiology and Public Health", Arch Pathol Lab Med, 2003, vol. 127, pp. 930-934.*
Yuan et al, Journal of Virology, (Jul. 2008), vol. 82, No. 13, pp. 6481-6491.*

* cited by examiner

*Primary Examiner*—Allison M Ford
(74) *Attorney, Agent, or Firm*—Norris McClaughlin

(57) ABSTRACT

A composition of lysozyme and a pharmaceutically acceptable carrier is active against the papilloma virus in both humans and animals. The composition can be used to treat women suffering from cervical cancer. The composition can also be used to treat cows and horses suffering sarcoids.

9 Claims, No Drawings

COMPOSITION AND METHOD FOR TREATING BOVINE PAPILLOMA VIRUS IN EQUINE

BACKGROUND OF THE INVENTION

1. Field of the Invention

The present invention relates generally to compositions useful for treating certain viral infections and pathological disorders caused thereby.

2. Description of Related Art

Papilloma virus, a sexually transmitted disease in human, is, among other things, the primary cause of cervical cancer. Current treatments for papilloma virus in humans depend on the type of papilloma virus involved. Thus, more than 100 different types of human papilloma virus exist. Recently a human vaccine has been introduced in the marketplace in order to protect against the strains that cause cervical cancer. In other mammals, such as bovine and equine species, papilloma virus (i.e. bovine and equine papilloma virus) constitutes a serious disease that produces large skin tumors, known as sarcoids. Currently, there is no effective permanent treatment for bovine or equine papilloma virus or sarcoids. Current therapies span from home made concoctions to chemotherapy to surgery. Seldom do any of these therapies prove successful, especially in the long run. Moreover, the use of chemotherapeutic drugs and surgery is very expensive. Accordingly, there remains a need in the art for new and effective treatments against papilloma virus infections in humans and animals, and against sarcoids.

Lysozyme is a known antiviral, which has shown strong action against gram-positive pathogens, such as the herpes virus in human and animal models. However, the action of lysozyme against papilloma virus, in particular, has not heretofore been described.

BRIEF SUMMARY OF THE INVENTION

It has surprisingly been discovered that lysozyme is effective in treating papilloma virus infections in humans and animals, and in treating sarcoids.

Accordingly, the present invention relates in a first embodiment to a composition for treating a papilloma virus infection in a mammal, wherein the composition comprises an antivirally effective amount of a lysozyme and a pharmaceutically acceptable carrier.

The present invention relates in a second embodiment to a method of treating a papilloma virus infection in a patient in need thereof by administering the inventive composition to the patient in an effective amount and for a period of time sufficient to treat the papilloma virus infection.

The present invention relates in a third embodiment to a method of treating sarcoids in a bovine or equine animal suffering therefrom comprising administering to the animal or topically applying to the sarcoids the inventive composition in an effective amount and for a period of time sufficient to treat the sarcoids.

DETAILED DESCRIPTION OF THE INVENTION

The inventive composition comprises a content of a lysozyme. The lysozyme can be naturally-occurring, synthetic or recombinant. In principal, all lysozymes are useful in the inventive composition, although the intended use of the inventive composition may suggest to those skilled in the art a preference for one type of lysozyme as opposed to another. In one preferred embodiment, the lysozyme is a human recombinant lysozyme, for example, as is disclosed in U.S. Pat. No. 6,991,824, the entire contents of which are hereby incorporated herein by reference. In another preferred embodiment, the lysozyme is a non-human lysozyme, especially a hen egg white lysozyme.

In a preferred embodiment, the inventive composition additionally comprises at least one additional therapeutic agent effective against papilloma virus. These additional therapeutic agents can be chemotherapeutic agents or other antiviral compounds. The lytic activity of lysozyme on the virus envelop can be expected to improve the effectiveness of such additional therapeutic agents.

Thus, the inventive composition can further comprise an effective amount of one or more antiviral agents, antiseptic agents, chemotherapeutic agents, immunopotentiating agents, or mixtures thereof. Preferably, the additional therapeutic agent is selected from the group consisting of acyclovir, vidarabine, uridine, 5-fluorouracil, thiotepa, interferons, podophyllotoxin, trichloroacetic acid, salicylic acid, carbamide peroxide, hexamethylene tetramine, cisplatin, and derivatives of each of the foregoing therapeutic agents. In one especially preferred embodiment, the additional therapeutic agent is acyclovir. In another especially preferred embodiment, the additional therapeutic agent is cisplatin. Generally, it has been shown that acyclovir and the other compounds mentioned are effective in reducing abnormal skin growth conditions [*Atlas, Microbiology, Fundamentals and Applications*, p 551, MacMillan, New York, London, (1984)]. In addition, 5-fluorouracil and thiotepa exhibit significant antineoplastic activities. The usage of podophyllotoxin, trichloroacetic acid, and salicylic acid is also documented in the treatment of HPV infections.

It is also known that interferons, which are released from infected cells, migrate to uninfected cells and protect them from viral infections [*Atlas, Microbiology, Fundamentals and Applications*, p. 481, MacMillan, New York, London, (1984)]. The activity of interferon on the cell lines of human papilloma virus (especially type 31) as manifested by growth arrest and apoptosis is also reported [Chang et al., *J. Virol.* 76: 8864-8874 (2002)]. Other antimicrobial, antiseptic and or oxygen donating agents, such as carbamide peroxide [Lim et al., *Cytotechnology* 31: 265-270 (1999)] or other germ killing compound generating agents such as hexamethylene tetramine can also help to eradicate viruses.

In an especially preferred embodiment, the inventive composition comprises a combination of lysozyme and one or more therapeutic agents selected from the group consisting of acyclovir, cisplatin vidarabine, uridine, 5-fluorouracil, thiotepa, interferons, podophyllotoxin, trichloroacetic acid, salicylic acid, carbamide peroxide, hexamethylene tetramine, and derivatives thereof, particularly acyclovir and cisplatin.

The inventive composition can be administered, orally, topically or by injection, intramuscular or intravenously. For this purpose, the inventive composition can be formulated in any suitable administration form. In a preferred embodiment, the inventive composition is in the form of tablets, capsules, lozenges, creams, lotions, powders, gels, or sprayable or injectable solutions. In one especially preferred embodiment, the inventive composition is in the form of a tablet, capsule or lozenge. In another especially preferred embodiment, the inventive composition is in the form of a solution. In another especially preferred embodiment, the inventive composition is in the form of a topical cream or lotion.

What is an "effective amount" of the various ingredients needs to be determined empirically depending on the end use and the mode of administration. In this regard, the lysozyme content can be varied over a wide range, preferably from about 0.01 to about 20% by weight of the inventive composition, especially from about 0.1 to about 7% by weight of the inventive composition, particularly from about 0.1 to about 5% by weight of the inventive composition. Additional therapeutic agents, where present, should be used at or below their normal recommended dosages and the entire inventive composition should ordinarily be administered according to the normal dosage regimens of such additional therapeutic agents.

The patient is either a human or an animal. In one preferred embodiment, the patient is a human, especially a woman suffering from or susceptible to cervical cancer. In a particularly preferred embodiment, the inventive formulation is administered to a woman suffering from or susceptible to cervical cancer in the form of an injectable solution. For this particular embodiment, the inventive formulation will be administered to such person typically once or twice daily for a period of days, weeks or months as necessary.

In another embodiment, the patient is a bovine or equine animal, for example, a cow or a horse. In a preferred embodiment, the patient is a cow or a horse, especially one suffering from or susceptible to sarcoids. In a particularly preferred embodiment, the cow or horse is suffering from sarcoids, and the lysozyme is administered to the cow or horse by topically applying a composition comprising the lysozyme to one or more of said sarcoids. In this embodiment, the inventive formulation most preferably comprises the lysozyme in the form of a sprayable solution or a cream or lotion. In this particular embodiment, the inventive formulation will be sprayed onto an area of the animal's skin covering the sarcoids once or twice daily for a period of days, weeks or months as necessary. In another particularly preferred embodiment, the cow or horse is suffering from sarcoids, and the lysozyme is administered to the cow or horse orally, for example, by a tablet or lozenge placed in the animal's mouth, or through the animal's drinking water or feed.

The invention will now be explained in greater detail with reference to the following non-limiting example.

EXAMPLE

A horse having large sarcoid tumors about its body was treated daily by applying copious amounts of a 5% lysozyme solution directly to skin areas covering the tumors. After a period of days, the tumors began to shrink, thereby showing the effectiveness of the lysozyme solution against such tumors.

It should be understood that the preceding detailed description of the invention is merely a detailed description of one preferred embodiment or of a small number of preferred embodiments of the present invention and that numerous changes to the disclosed embodiment(s) can be made in accordance with the disclosure herein without departing from the spirit or scope of the invention. The preceding detailed description of the invention, therefore, is not meant to limit the scope of the invention in any respect. Rather, the scope of the invention is to be determined only by the appended issued claims and their equivalents.

What is claimed is:

1. A method of treating bovine papilloma virus infection in an equine animal suffering from sarcoids, said method comprising administering to said equine animal an effective amount therefor of a lysozyme for a period of time sufficient to treat said bovine papilloma virus infection.

2. The method according to claim 1, wherein the lysozyme is administered to the equine animal by topically applying a composition comprising the lysozyme to an area of the equine animal's skin covering one or more of said sarcoids.

3. The method according to claim 2, wherein the composition comprising the lysozyme is in the form of a sprayable solution or a cream or lotion.

4. The method according to claim 3, wherein the composition additionally comprises cisplatin.

5. The method according to claim 1, wherein the lysozyme is administered orally to the animal.

6. The method according to claim 5, wherein the lysozyme is administered orally to the equine animal in combination with cisplatin.

7. The method according to claim 1, wherein the equine animal is a horse.

8. A method of shrinking the size of sarcoid tumors in an equine animal suffering from sarcoid tumors, said method comprising administering an effective amount therefor of a lysozyme for a period of time sufficient to shrink said sarcoid tumors.

9. The method according to claim 8, wherein the equine animal is a horse.

* * * * *